(12) United States Patent
Kim

(10) Patent No.: US 10,874,445 B2
(45) Date of Patent: Dec. 29, 2020

(54) SCREW FIXING APPARATUS

(71) Applicant: KYUNGPOOK NATIONAL UNIVERSITY INDUSTRY-ACADEMIC COOPERATION FOUNDATION, Daegu (KR)

(72) Inventor: Kyoung Tae Kim, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 338 days.

(21) Appl. No.: 15/017,837

(22) Filed: Feb. 8, 2016

(65) Prior Publication Data

US 2017/0100177 A1    Apr. 13, 2017

Related U.S. Application Data

(60) Provisional application No. 62/240,825, filed on Oct. 13, 2015.

(51) Int. Cl.
*A61B 17/86* (2006.01)
*A61B 17/68* (2006.01)
*A61B 17/70* (2006.01)

(52) U.S. Cl.
CPC ........ *A61B 17/8685* (2013.01); *A61B 17/686* (2013.01); *A61B 17/7032* (2013.01); *A61B 17/864* (2013.01); *A61B 2017/8655* (2013.01)

(58) Field of Classification Search
CPC . A61B 17/844; A61B 17/864; A61B 17/8685; A61B 17/869; A61B 2017/8655; F16B 13/124
USPC .................. 606/313, 314; 411/55, 80.5, 80.6
See application file for complete search history.

(56) References Cited

U.S. PATENT DOCUMENTS

| | | | |
|---|---|---|---|
| 4,027,932 A | 6/1977 | Kunkel et al. | |
| 4,359,318 A | 11/1982 | Gittleman | |
| 4,474,516 A | 10/1984 | Schiefer | |
| 4,678,383 A | 7/1987 | Bergner | |
| 5,127,407 A | 7/1992 | Tan | |
| 5,265,504 A | 11/1993 | Fruhm | |
| 6,171,311 B1 | 1/2001 | Richelsoph | |
| 6,249,946 B1 | 6/2001 | Greenhill | |
| 6,258,089 B1 | 7/2001 | Campbell et al. | |
| 6,290,701 B1 | 9/2001 | Enayati | |
| 6,331,179 B1 | 12/2001 | Freid et al. | |
| 6,402,757 B1 | 6/2002 | Moore, III et al. | |
| 6,436,100 B1 | 8/2002 | Berger | |
| 6,652,525 B1 | 11/2003 | Assaker et al. | |
| 6,767,350 B1 | 7/2004 | Lob | |

(Continued)

FOREIGN PATENT DOCUMENTS

JP    2011-139901 A    7/2011
JP    2014-517739 A    7/2014

(Continued)

*Primary Examiner* — Amy R Sipp
(74) *Attorney, Agent, or Firm* — Novick, Kim & Lee, PLLC; Sang Ho Lee

(57) ABSTRACT

A screw fixing apparatus includes a screw inserted into a human body, and a screw anchor having an insertion hole that receives the screw. The screw anchor is inserted into the human body and the screw is inserted into the human body.

9 Claims, 3 Drawing Sheets

(56) References Cited

U.S. PATENT DOCUMENTS

| | | | |
|---|---|---|---|
| 6,778,861 B1 | 8/2004 | Liebrecht et al. | |
| 7,029,472 B1 | 4/2006 | Fortin | |
| 7,194,314 B1 | 3/2007 | Richter et al. | |
| 7,235,100 B2 | 6/2007 | Martinek | |
| 7,302,298 B2 | 11/2007 | Lowry et al. | |
| 7,662,154 B2 | 2/2010 | Ribeiro | |
| 8,057,521 B2 | 11/2011 | Smisson, III et al. | |
| 8,419,777 B2 | 4/2013 | Walker et al. | |
| 8,454,667 B2 | 6/2013 | Humphreys | |
| 8,628,325 B2 | 1/2014 | Vachtenberg | |
| 8,758,347 B2 | 6/2014 | Weiner et al. | |
| 8,906,077 B2 | 12/2014 | Bush, Jr. et al. | |
| 8,932,335 B2 | 1/2015 | Humphreys | |
| 8,940,030 B1 | 1/2015 | Stein et al. | |
| 8,956,394 B1 * | 2/2015 | McDonnell | A61B 17/686 606/300 |
| 9,265,531 B2 | 2/2016 | Ziolo | |
| 9,629,664 B2 | 4/2017 | Altarac et al. | |
| 9,775,652 B2 | 10/2017 | Altarac et al. | |
| 9,918,749 B2 | 3/2018 | Altarac et al. | |
| 9,918,760 B2 | 3/2018 | Bush, Jr. et al. | |
| 9,943,341 B2 | 4/2018 | Carnes | |
| 2002/0040241 A1 * | 4/2002 | Jarvinen | A61F 2/0811 623/13.14 |
| 2002/0151899 A1 | 10/2002 | Bailey et al. | |
| 2003/0135274 A1 * | 7/2003 | Hays | A61F 2/0811 623/13.14 |
| 2003/0187440 A1 | 10/2003 | Richelsoph et al. | |
| 2004/0220571 A1 | 11/2004 | Assaker et al. | |
| 2004/0243207 A1 | 12/2004 | Olson et al. | |
| 2004/0267361 A1 * | 12/2004 | Donnelly | A61F 2/0811 623/13.14 |
| 2005/0059972 A1 | 3/2005 | Biscup | |
| 2005/0192577 A1 | 9/2005 | Mosca et al. | |
| 2005/0216027 A1 | 9/2005 | Suh | |
| 2005/0261689 A1 | 11/2005 | Lin | |
| 2006/0106390 A1 | 5/2006 | Jensen et al. | |
| 2006/0149258 A1 * | 7/2006 | Sousa | A61F 2/0811 623/13.12 |
| 2006/0161157 A1 | 7/2006 | Mosca et al. | |
| 2006/0217721 A1 | 9/2006 | Suh | |
| 2006/0235410 A1 | 10/2006 | Ralph et al. | |
| 2006/0247639 A1 | 11/2006 | Anderson | |
| 2006/0293670 A1 | 12/2006 | Smisson et al. | |
| 2007/0233071 A1 | 10/2007 | Dewey et al. | |
| 2008/0039846 A1 | 2/2008 | Lee | |
| 2008/0161864 A1 * | 7/2008 | Beck | A61F 2/0811 606/326 |
| 2008/0188897 A1 | 8/2008 | Krebs et al. | |
| 2008/0221624 A1 | 9/2008 | Gooch | |
| 2009/0125072 A1 | 5/2009 | Neubardt | |
| 2009/0318970 A1 | 12/2009 | Butler et al. | |
| 2010/0036467 A1 | 2/2010 | Kraus et al. | |
| 2010/0049256 A1 | 2/2010 | Jeon et al. | |
| 2010/0106198 A1 | 4/2010 | Adcox et al. | |
| 2010/0121383 A1 | 5/2010 | Stanaford et al. | |
| 2011/0022097 A1 | 1/2011 | Walker et al. | |
| 2011/0029023 A1 | 2/2011 | Tornier | |
| 2011/0106159 A1 | 5/2011 | Nazeck | |
| 2011/0144702 A1 | 6/2011 | Leroux et al. | |
| 2011/0152934 A1 | 6/2011 | Asaad et al. | |
| 2011/0230885 A1 | 9/2011 | Weiner et al. | |
| 2011/0264151 A1 | 10/2011 | Davis et al. | |
| 2012/0185001 A1 | 7/2012 | Nayet et al. | |
| 2012/0232595 A1 | 9/2012 | Holschlag | |
| 2012/0265258 A1 * | 10/2012 | Garvey | A61B 17/8685 606/315 |
| 2012/0271363 A1 | 10/2012 | Luxon et al. | |
| 2012/0289978 A1 | 11/2012 | Jacob | |
| 2013/0023936 A1 | 1/2013 | Altarac et al. | |
| 2013/0041413 A1 | 2/2013 | Sun | |
| 2013/0231704 A1 | 9/2013 | Larroque-Lahitette | |
| 2013/0304067 A1 | 11/2013 | Hess et al. | |
| 2013/0325074 A1 | 12/2013 | Ziolo | |
| 2014/0066997 A1 | 3/2014 | Humphreys | |
| 2015/0134013 A1 | 5/2015 | Paul | |
| 2015/0201982 A1 | 7/2015 | Altarac et al. | |
| 2015/0216573 A1 | 8/2015 | Chin et al. | |
| 2015/0230838 A1 | 8/2015 | Lazoglu et al. | |
| 2016/0166295 A1 | 6/2016 | Ziolo | |
| 2016/0206351 A1 | 7/2016 | Eom | |
| 2016/0278834 A1 | 9/2016 | Bayer | |

FOREIGN PATENT DOCUMENTS

| | | |
|---|---|---|
| KR | 1999-0035953 A | 5/1999 |
| KR | 10-2002-0082009 A | 10/2002 |
| KR | 1020040001287 A | 1/2004 |
| KR | 20-0367241 Y1 | 11/2004 |
| KR | 10-2005-0023111 A | 3/2005 |
| KR | 10-2007-0026472 A | 3/2007 |
| KR | 10-2007-0112200 A | 11/2007 |
| KR | 10-2008-0059920 A | 7/2008 |
| KR | 10-0850322 B1 | 8/2008 |
| KR | 10-2008-0105506 A | 12/2008 |
| KR | 10-0872529 B1 | 12/2008 |
| KR | 10-2009-0015933 A | 2/2009 |
| KR | 10-2009-0111774 A | 10/2009 |
| KR | 10-2010-0124709 A | 11/2010 |
| KR | 10-2012-0039622 A | 4/2012 |
| KR | 10-2012-0040309 A | 4/2012 |
| KR | 10-2012-0052265 A | 5/2012 |
| KR | 10-1142895 B1 | 5/2012 |
| KR | 10-2012-0057758 A | 6/2012 |
| KR | 10-2013-0004669 A | 1/2013 |
| KR | 10-2013-0015081 A | 2/2013 |
| KR | 10-2013-0016303 A | 2/2013 |
| KR | 10-1331429 B1 | 11/2013 |
| KR | 10-2014-0003938 A | 1/2014 |
| KR | 10-2014-0018796 A | 2/2014 |
| KR | 10-2014-0052320 A | 5/2014 |
| KR | 10-1413732 B1 | 7/2014 |
| KR | 10-2015-0120105 A | 10/2015 |
| WO | 2008/146981 A1 | 12/2008 |
| WO | 2009/105106 A2 | 8/2009 |

* cited by examiner

SCREW FIXING APPARATUS

CROSS-REFERENCE TO RELATED APPLICATION

This application claims the benefit of U.S. Provisional Patent Application No. 62/240,825, filed on Oct. 13, 2015, the disclosure of which is incorporated herein by reference in its entirety.

BACKGROUND

1. Field of the Invention

The present invention relates to a screw fixing apparatus, and more particularly, to a screw fixing apparatus capable of improving a fixing force of a screw inserted into a human body.

2. Discussion of Related Art

In general, diseases related to the vertebral column are treated using indirect treatment methods such as physical therapy or direct treatment methods which correct and fix the vertebral column by additionally installing fixation apparatuses at the damaged vertebral portion.

That is, when vertebral diseases are minor, physical therapy is performed, but, when diseases of the cervical vertebrae, thoracic vertebrae, lumbar vertebrae, sacrum, intervertebral discs, and the like which constitute the vertebral column are serious, treatments using additional vertebral fixing apparatuses are performed.

A vertebral fixing apparatus conventionally used includes a vertebral pedicle (sacrum) screw inserted into a vertebral pedicle or the sacrum at a predetermined angle and depth, a vertebral rod positioned at one side of a vertebral portion, and a fixing cap or coupling portion which connects and couples the vertebral rod and the vertebral pedicle screw.

Meanwhile, the vertebral column is formed with thirty two to thirty five vertebrae forming a torso and intervertebral discs between the vertebrae, supports the truncus, and connects a skull at an upper end and a pelvis at a lower end thereof. The vertebral column has, from the top thereof, seven cervical vertebrae, twelve thoracic vertebrae, five lumbar vertebrae, five sacral vertebrae, three to five coccygeal vertebrae. An adult has a sacrum in which five sacral vertebrae are fused, and a coccyx including three to five coccygeal vertebrae.

Particularly, the vertebra includes one vertebral body, two pedicles, two laminae, a spinous process at the rear thereof, and two transverse processes and upper and lower articular processes at both sides thereof.

So to treat a damaged vertebral portion, first, a pedicle screw is inserted into and fixed to a vertebral pedicle or the sacrum in a suitable direction and at a suitable position, the vertebral portion is corrected into a normal state using a vertebral rod, and the vertebral rod and a fixing screw are fixed using a fixing cap or coupling portion to complete the treatment.

In the case of open surgery in which a diseased section of a patient with at least the longitudinal length of a vertebral fixing apparatus is cut out, because the diseased part is enlarged, more time is needed to suture the diseased part section, and the surgical scar of the diseased part of the patient after the surgical treatment may be enlarged.

Basically, the activity of vertebral muscles, particularly the erector spinae muscles, is directly related to a posture of the trunk, and the pelvis, and is also related to the function of the trunk muscle and a lower back disorder. Particularly, degeneration of an adjacent segment after surgical treatment means that a bad result after the vertebral surgery is related to a posture which is modified and distorted.

In the case of a surgical operation, since the muscles and nervous tissues are cut and removed, a negative surgical result may occur due to the inactivity of the trunk muscles, and an increased load which increases the pressure and amount of shear stress applied to intervertebral discs. This may result in the degeneration of the discs.

Recently, diseases related to not only a vertebral column but also a bone have been increased due to the increasingly aging population, and related studies have been conducted.

For example, a vertebral fixing apparatus was disclosed in the prior art No. 2006-0133857 applied at Dec. 26, 2006.

SUMMARY OF THE INVENTION

The present invention is directed to a screw fixing apparatus capable of improving a fixing force of a screw in a bone when a screw loosening phenomenon occurs around the screw due to the halo phenomenon after the screw is inserted.

The present invention is directed to a screw fixing apparatus screw in which a screw anchor is provided of a plastic material such that when a screw is inserted into the screw anchor, an inner space of the screw anchor is expanded, a connection portion formed between holes of the screw anchor is disconnected, and thus a fixing force of the screw is improved.

The present invention is directed to a screw fixing apparatus in which a pitch of a screw thread of a screw matches a pitch of a screw thread of a screw anchor such that when the screw is inserted into the screw anchor, the damage to the screw anchor is prevented.

The present invention is directed to a screw fixing apparatus in which protrusions are provided on an outer surface of a screw anchor such that the coefficient of friction between the screw anchor and a bone surface is increased and sufficient pull-out strength is obtained.

The present invention is directed to a screw fixing apparatus in which protrusions formed on an outer surface of a screw anchor are provided with a predetermined directionality such that a screw inserted into the screw anchor is prevented from being separated from a bone.

The present invention is directed to a screw fixing apparatus capable of using screws having various sizes.

The present invention is directed to a screw fixing apparatus which is simply manufactured comparatively and easily applied to a surgical operation.

According to an aspect of the present invention, there is provided a screw fixing apparatus including a screw inserted into a human body and a screw anchor in which an inner space is formed such that the screw is inserted into the screw anchor, wherein the screw anchor is inserted into the human body before the screw is inserted into the human body to prevent the loosening of the screw.

An insertion hole may be formed at one end of the screw anchor to insert the screw into the screw anchor, and the inner space may be formed in a lengthwise direction of the screw anchor.

The inner space of the screw anchor may be expanded when the screw is inserted into the screw anchor.

A screw thread may be formed on the surface of the inner space of the screw anchor, and a pitch of the screw thread formed in the screw anchor may correspond to a pitch of a screw thread formed on the screw.

A protrusion which improves the pull-out strength of the screw anchor may be formed from an outer surface of the screw anchor, and the protrusion may be formed to be inclined toward an end portion of the screw anchor into which the screw is inserted.

The protrusion may be formed from the outer surface of the screw anchor in a lengthwise direction of the screw anchor.

A plurality of holes may be formed in the screw anchor, and the plurality of holes may be formed from the outer surface of the screw anchor toward an inner space of the screw anchor.

The plurality of holes may be separately disposed in a lengthwise direction of the screw anchor.

Connection portions may be provided between the plurality of holes, and the plurality of holes may be connected by the connection portions.

The connection portion may be disconnected due to an insertion force of the screw in the screw anchor.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
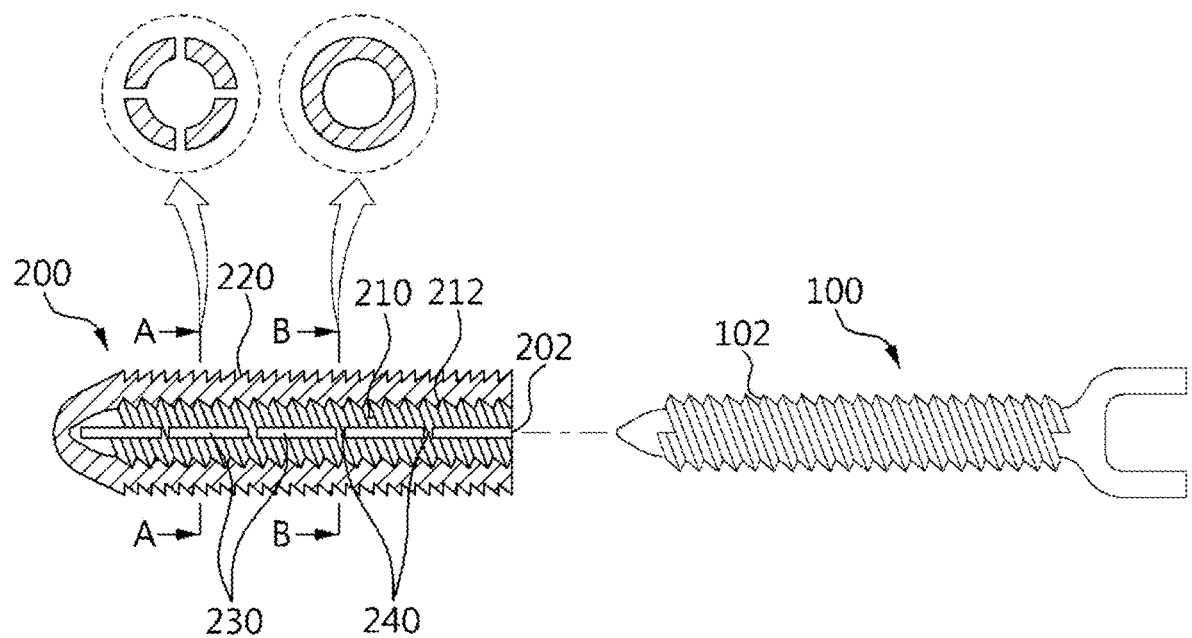
FIG. 1 is a side view illustrating a screw fixing apparatus according to one embodiment of the present invention.

Embodiments of the present invention will be described in detail with reference to the accompanying drawings. However, the present invention is not limited to the embodiments. Like reference numerals in the drawings denote like elements.

Figure 2:
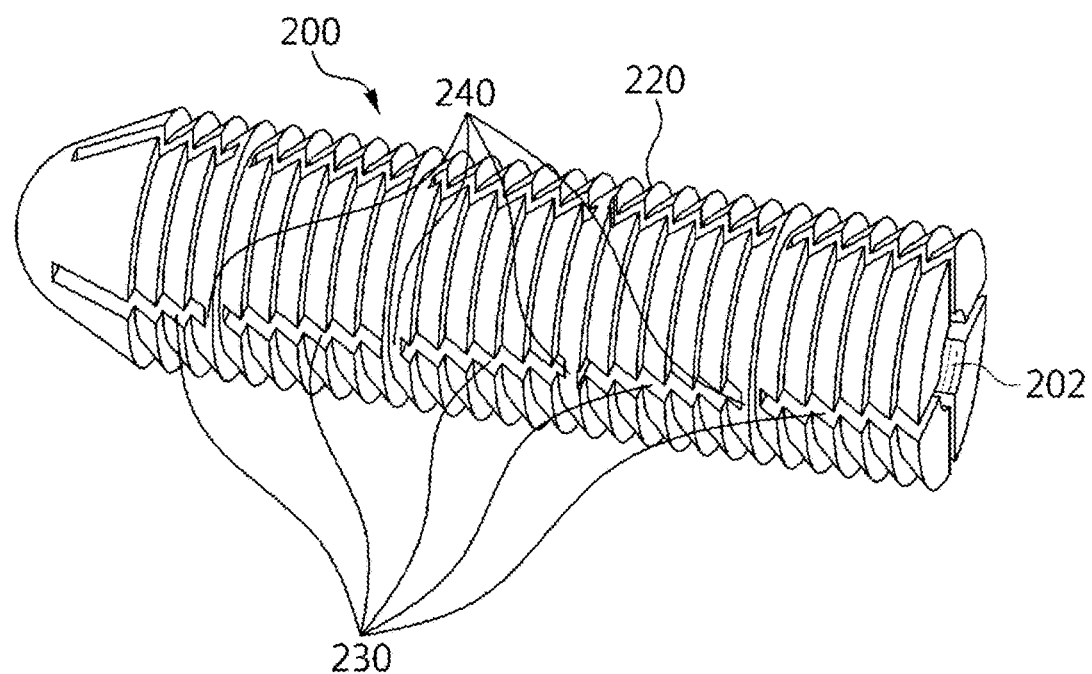
FIG. 2 is a perspective view illustrating a screw anchor in the screw fixing apparatus according to one embodiment of the present invention.
Figure 3:
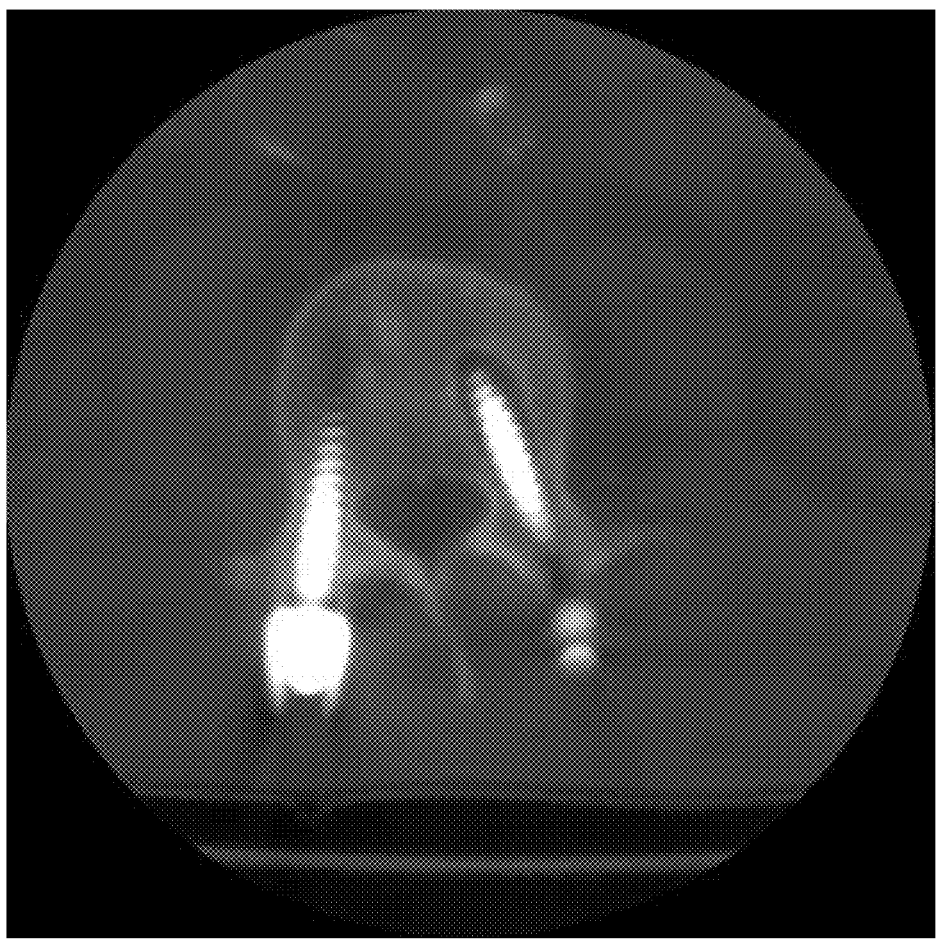
FIG. 3 is a view for showing a screw loosening phenomenon.
Figure 4:
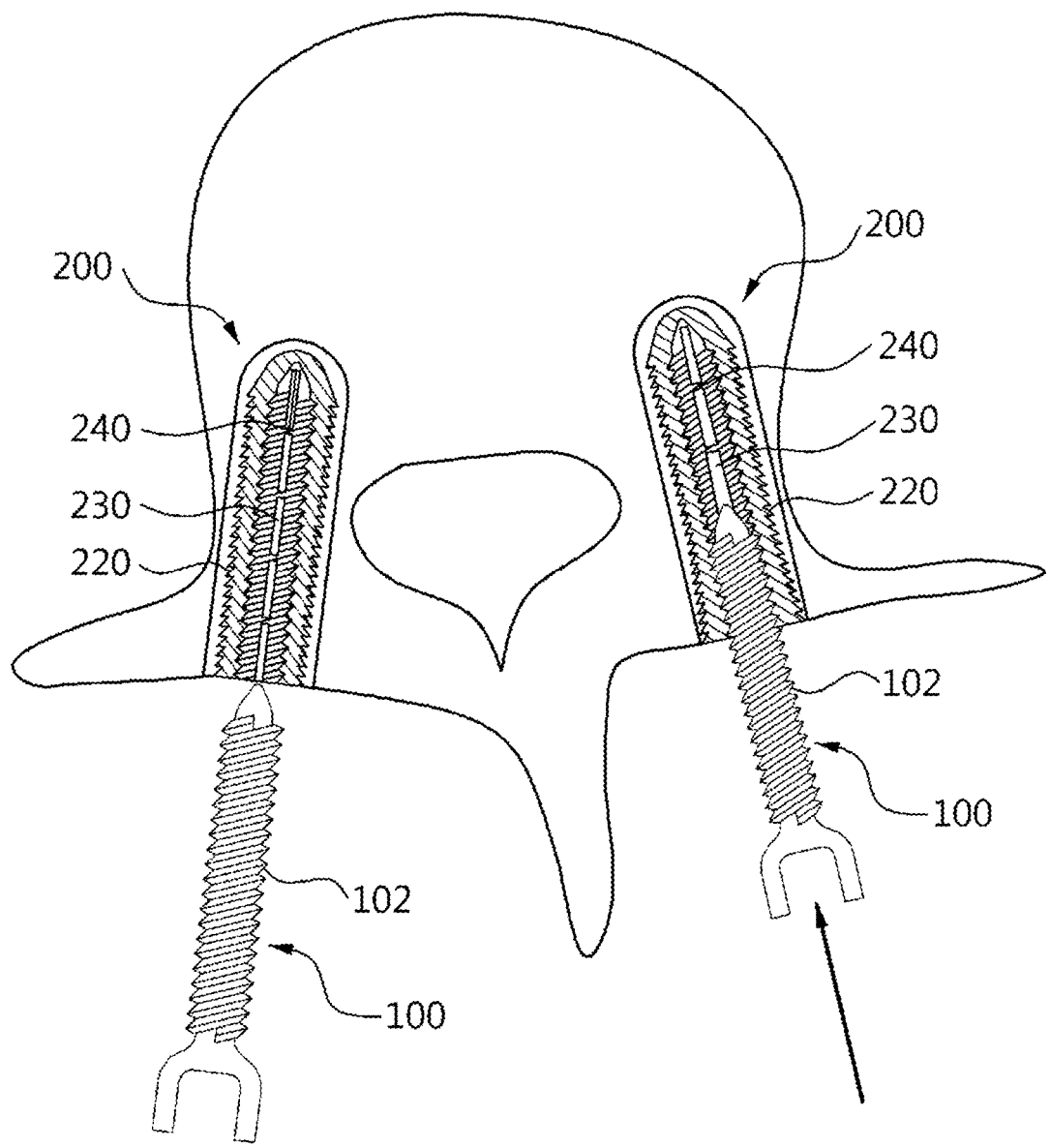
FIG. 4 is a view of a screw being inserted into the screw anchor in the screw fixing apparatus according to one embodiment of the present invention.

FIG. 1 is a side view illustrating a screw fixing apparatus according to one embodiment of the present invention, FIG. 2 is a perspective view illustrating a screw anchor in the screw fixing apparatus according to one embodiment of the present invention, FIG. 3 is a view for showing a screw loosening phenomenon, and FIG. 4 is a view of a screw being inserted into the screw anchor in the screw fixing apparatus according to one embodiment of the present invention.

Referring to FIG. 1, the screw fixing apparatus 10 according to one embodiment of the present invention may include the screw 100 and the screw anchor 200.

The screw 100 may be inserted into a human body.

Specifically, the screw 100 may be inserted into a vertebra, a tooth or a muscle, and the like. Hereinafter, the screw 100 which is used in a screw fixing method for treating a disease related to a bone is exemplified and described.

For example, since a vertebra is unstable after a laminectomy, a screw fixing method may firmly fix the vertebra by inserting a screw into the vertebra.

Thus, the screw 100 may be manufactured of a titanium material which has excellent biocompatibility and strength and is used as a material for various types of implants.

However, the material of the screw 100 may not be limited thereto, and various materials may be provided for the screw 100.

The screw 100 may have a predetermined length, two branches which extend lengthwise may be formed at an end of the screw 100, and the screw 100 may be tightened or loosened by inserting a driver (not shown) between the two branches.

In addition, a screw thread 102 may be formed on an outer surface of the screw 100.

Since the screw thread 102 is for coupling the screw 100 to a screw anchor 200, a pitch of the screw thread 102 formed at the screw 100 may match a pitch of a screw thread 212 formed in the screw anchor 200.

The above-described screw 100 may be inserted into the screw anchor 200.

The screw anchor 200 may also be inserted into the human body as well as the screw 100.

Specifically, after the screw anchor 200 is first inserted into a widened space in a bone, the screw 100 may be inserted into the screw anchor 200.

This is to prevent a loosening phenomenon of the screw 100. For example, this is to prevent the screw 100 from being separated from the bone.

Particularly, referring to FIG. 2, the screw anchor 200 may be constituted as follows.

The screw anchor 200 may be provided of a plastic material such as polymethyl methacrylate (PMMA).

Thus, when the screw 100 is inserted into the screw anchor 200, the screw anchor 200 is expanded and the screw anchor 200 fills the widened space, and thus a fixing force of the screw 100 may be improved.

The screw anchor 200 may have a predetermined length, and one end of the screw anchor 200 may be provided to have a conical shape for facilitating the insertion into the bone.

In addition, an insertion hole 202 for an insertion of the screw 100 may be formed in the screw anchor 200.

The insertion hole 202 may be formed at one end of the screw anchor 200, and the insertion hole 202 may have a size that the screw 100 is insertable thereinto.

The screw 100 may be guided to an inner space 210 of the screw anchor 200 through the insertion hole 202 of the screw anchor 200.

The inner space 210 may be formed to extend from one end of the screw anchor 200 in which the insertion hole 202 is formed toward the other end of the screw anchor 200 in a lengthwise direction of the screw anchor 200.

In addition, the inner space 210 may be widened due to an insertion force of the screw 100.

This is because of the above-described material of the screw anchor 200.

Specifically, while the screw 100 is being inserted into the inner space 210 of the screw anchor 200, the inner space 210 of the screw anchor 200 is widened due to the insertion force of the screw 100, and thus a diameter of the screw anchor 200 may be enlarged, and the screw anchor 200 may fill a widened hole in the bone.

The screw thread 212 may be formed on a surface of the inner space 210. The screw thread 212 may be screw coupled to the screw thread 102 of the above-described screw 100.

In addition, a pitch of the screw thread 212 formed at the inner space 210 may match the pitch of the screw thread 102 formed on the screw 100.

Accordingly, when the screw 100 is inserted into the inner space 210, a part of the screw anchor 200 may be prevented from being broken, and the fixing force of the screw 100 in the screw anchor 200 may be maintained.

At this time, the fixing force of the screw 100 in the screw anchor 200 may represent the fixing force of the screw 100 in an inside of the human body, for example, the bone.

In addition, protrusions 220 may be formed on an outer surface of the screw anchor 200.

The protrusion 220 may be formed to have predetermined directionality.

Specifically, the protrusions 220 may be formed toward an end portion of the screw anchor 200 in which the screw 100 is inserted and formed to be inclined toward the insertion hole 202 of the screw anchor 200.

Here, the protrusions 220 may be formed from the outer surface of the screw anchor 200 in a lengthwise direction of the screw anchor 200.

For example, the protrusions 220 may be formed on the entire surface of the outer surface of the screw anchor 200. However, the protrusions 220 may not be limited thereto, the protrusions 220 may be formed from the outer surface of the screw anchor 200 at both sides facing each other in a lengthwise direction of the screw anchor 200 or may be formed on a part of the outer surface of the screw anchor 200.

Accordingly, the coefficient of friction between the screw anchor 200 and a surface of a bone may be increased and sufficient pull-out strength may be obtained.

In addition, since the protrusions 220 have a constant directionality, the screw 100 inserted into the screw anchor 200, as well as the screw anchor 200 may be prevented from being separated from a bone.

In addition, a hole 230 may be formed in the screw anchor 200.

The hole 230 may be formed from the outer surface of the screw anchor 200 toward the inner space 210 of the screw anchor 200.

Here, the hole 230 may be formed in a plural number.

The plurality of holes 230 may be separately disposed in a lengthwise direction of the screw anchor 200.

For example, four holes 230 may be formed, and the four holes 230 may be provided to have a rectangular cross-section in a lengthwise direction of the inner space 210 and may be disposed linearly.

However, a shape and a displacement of the holes may not be limited thereto, and the holes may be provided to have various shapes.

For example, the hole 230 may be provided in a number which is not four, and the shape of the hole 230 may be a circular or polygonal shape. In addition, the plurality of holes 230 may be radially disposed in a lengthwise direction of the inner space 210.

In addition, when the protrusions 220 are formed at a part of the screw anchor 200, the hole 230 may be formed at a portion in which the protrusions 220 are not formed in the screw anchor 200.

Connection portions 240 may be provided between the above described plurality of holes 230.

The plurality of holes 230 may be connected by the connection portions 240.

The connection portions 240 may be integrally provided with the screw anchor 200, or may be provided as separate elements from the screw anchor 200.

When the connection portions 240 are integrally provided with the screw anchor 200, intervals between the plurality of holes 230 may be the connection portions 240.

However, when the connection portions 240 are separately provided from the screw anchor 200, the connection portions 240 may be provided to have any structure or material as long as the connection portions 240 are disconnected due to the insertion force of the screw 100 when the screw 100 is inserted into the screw anchor 200.

Specifically, when the screw 100 is inserted into the inner space 210 of the screw anchor 200 to expand the inner space 210, the intervals between the plurality of holes 230 may be expanded, and thus the connection portion 240 may be disconnected.

Accordingly, coupling between the screw 100 and the screw anchor 200 may become firm, and thus the fixing force of the screw 100 and the screw anchor 200 in a bone may be improved.

Here, a size of the screw 100 does not need to exactly match a size of the inner space 210 of the screw anchor 200, the size of the screw 100 may be provided slightly greater than that of the inner space 210 of the screw anchor 200.

Thus, a screw 100 having various sizes may be used.

Particularly, as illustrated in FIG. 3, the screw 100 may lose the fixing force in a bone.

Specifically, as time passes after a screw fixing treatment is performed, a bone adjacent to a screw fixed to the bone may be dissolved. This is referred to as a halo, that is, a bone halo phenomenon, and accordingly, a screw loosening phenomenon occurs.

Accordingly, approximately half of the patients into whom a screw is inserted may have future degeneration of an adjacent segment due to a screw fixing treatment, and a situation in which an upper segment or a lower segment near the operated segment is reoperated on due to emergent problems may occur.

In this case, a larger screw may be inserted, a bone around the screw may be filled with cement or the like, or an allograft bone plug may be placed, at a position in which the screw loosening phenomenon occurs. However, a firm fixing force of the screw in the bone is difficult to obtain through the above-described method.

The screw fixing apparatus 10 according to one embodiment of the present invention may improve the fixing force of the screw 100 and the screw anchor 200 in a bone due to a coupling structure of the screw 100 and the screw anchor 200.

Referring to FIG. 4, the screw fixing apparatus 10 according to one embodiment of the present invention may be applied to a screw fixing treatment as follows.

First, the screw anchor 200 is inserted into an expanded hole in a bone.

Here, since the protrusions 220 formed on an outer surface of the screw anchor 200 is provided to have the constant directionality, the protrusion 220 is inserted into the expanded hole in the bone, and the screw anchor 200 is prevented from being separated from the bone.

Next, the screw 100 is inserted into the inner space 210 of the screw anchor 200.

Since the pitch of the screw thread 212 formed at the inner space 210 of the screw anchor 200 matches the pitch of the screw thread 102 formed on the screw 100, when the screw 100 is inserted into the screw anchor 200, the screw anchor 200 may be prevented from being broken.

When the screw 100 is inserted into the screw anchor 200, the inner space 210 of the screw anchor 200 widens.

Accordingly, the hole 230 formed in the screw anchor 200 widens, and thus the connection portions 240 between the holes 230 are disconnected due to the insertion force of the screw 100.

Accordingly, the screw 100 may be firmly fixed to an inside of the screw anchor 200, and the widened screw anchor 200 may be pressed against the widened hole in the bone.

Accordingly, when the screw is inserted into the bone and the screw loosening phenomenon occurs due to a bone halo phenomenon adjacent to the screw, the screw fixing apparatus according to one embodiment of the present invention may improve the fixing force of the screw in the bone, and since the screw anchor is provided of the plastic material, when the screw is inserted into the screw anchor, the inner space of the screw anchor may be expanded, the connection portions formed between the holes of the screw anchor may be disconnected, and thus the fixing force of the screw may be improved. In addition, as the protrusions are provided on the outer surface of the screw anchor to increase the coefficient of friction between the screw anchor and a bone surface, the sufficient pull-out strength may be obtained, a screw having various sizes may be used, a manufacturing thereof may be simplified, and thus the screw anchor may be easily applied to an operation.

As described above, a screw fixing apparatus according to one embodiment of the present invention can improve a fixing force of a screw in a bone when a screw loosening phenomenon occurs around the screw due to a halo phenomenon after the screw is inserted thereinto.

According to a screw fixing apparatus according to one embodiment of the present invention, as a screw anchor is provided of a plastic material, when a screw is inserted into the screw anchor, an inner space of the screw anchor is expanded, connection portions formed between holes of the screw anchor is disconnected, and thus a fixing force of the screw can be improved.

According to a screw fixing apparatus according to one embodiment of the present invention, as the pitch of a screw thread of a screw matches a pitch of a screw thread of a screw anchor, when the screw is inserted into the screw anchor, damage to the screw anchor can be prevented.

According to a screw fixing apparatus according to one embodiment of the present invention, as protrusions are provided on an outer surface of a screw anchor, the coefficient of friction between the screw anchor and the bone surface is increased, and thus sufficient pull-out strength can be obtained.

According to a screw fixing apparatus according to one embodiment of the present invention, as protrusions formed on an outer surface of a screw anchor have a predetermined directionality, a screw inserted into the screw anchor can be prevented from being separated from a bone.

A screw fixing apparatus according to one embodiment of the present invention can use a screw having various sizes.

A screw fixing apparatus according to one embodiment of the present invention can be simply manufactured comparatively, and can be applied to a surgical operation.

While the embodiment of the present invention has been described with reference to specific details such as detailed components, specific embodiments and drawings, these are only examples to facilitate overall understanding of the invention and the invention is not limited thereto. It will be understood by those skilled in the art that various modifications and alterations may be made. Therefore, the spirit and scope of the invention are defined not by the detailed description of the invention but by the appended claims, and encompasses all modifications and equivalents that fall within the scope of the appended claims.

What is claimed is:

1. A screw fixing apparatus comprising:
a screw configured to be inserted into a human body; and
a screw anchor having an insertion hole that receives the screw,
wherein the screw anchor is configured to be inserted into the human body,
wherein at least one protrusion is located at an outer circumferential surface of the screw anchor,
wherein a distal end of the screw anchor has a protrusion-free tapered surface,
wherein a plurality of through-holes are defined collinearly in a longitudinal direction of the screw anchor through the at least one protrusion,
wherein the distal end of the screw anchor forms a closed distal tip and a distal through-hole of the plurality of through-holes extends continuously from within the at least one protrusion, through the protrusion-free tapered surface, towards the closed distal tip such that the distal through-hole terminates prior to the closed distal tip and within the protrusion-free tapered surface,
wherein at least one connection portion is located between adjacent collinear through-holes of the plurality of through-holes, and
wherein the at least one connection portion of the screw anchor forms a circumferential portion of the outer circumferential surface of the screw anchor and is configured to be broken in response to a predetermined insertion force of the screw.

2. The screw fixing apparatus of claim 1, wherein the insertion hole having an elongated shape along the longitudinal direction of the screw anchor is defined coaxial to the screw anchor.

3. The screw fixing apparatus of claim 1, wherein the insertion hole of the screw anchor is elastic for expansion as the screw is inserted into the screw anchor.

4. The screw fixing apparatus of claim 1, wherein an anchor screw thread is positioned on an inner surface of the insertion hole of the screw anchor, and a pitch of the anchor screw thread corresponds to a pitch of a screw thread of the screw.

5. The screw fixing apparatus of claim 1, wherein the at least one protrusion is inclined toward a direction that the screw is inserted from.

6. The screw fixing apparatus of claim 1, wherein the plurality of through-holes and the at least one connection portion form a line in the longitudinal direction of the screw anchor.

7. The screw fixing apparatus of claim 6, wherein the plurality of through-holes and the at least one connection portion form a plurality of lines which are extended in the longitudinal direction of the screw anchor.

8. The screw fixing apparatus of claim 7, wherein each of the plurality of through-holes has a length; and wherein the length of each of the plurality of through-holes is substantially the same.

9. The screw fixing apparatus of claim 6, wherein each of the plurality of through-holes has a length; and wherein the length of each of the plurality of through-holes is substantially the same.

* * * * *